(12) United States Patent
Sasagawa et al.

(10) Patent No.: US 8,741,941 B2
(45) Date of Patent: Jun. 3, 2014

(54) ANTIFUNGAL MEDICINAL COMPOSITIONS (75) Inventors: Hideaki Sasagawa, Yokohama (JP); Madoka Ito, Yokohama (JP); Takuji Nakashima, Yokohama (JP); Akira Nozawa, Yokohama (JP)

(73) Assignee: Pola Pharma Inc., Tokyo (JP)

( * ) Notice: Subject to any disclaimer, the term of this patent is extended or adjusted under 35 U.S.C. 154(b) by 67 days.

(21) Appl. No.: 13/240,833

(22) Filed: Sep. 22, 2011

(65) Prior Publication Data
US 2012/0015996 A1    Jan. 19, 2012

Related U.S. Application Data (63) Continuation of application No. 10/518,776, filed as application No. PCT/JP03/07367 on Jun. 10, 2003, now Pat. No. 8,039,452.

(30) Foreign Application Priority Data
Jun. 18, 2002   (JP) ................ 2002-177060

(51) Int. Cl.
A01N 43/50   (2006.01)
A61K 31/415  (2006.01)
A01N 43/26   (2006.01)
A61K 31/385  (2006.01)
A61F 13/00   (2006.01)
A61K 9/70    (2006.01)

(52) U.S. Cl.
USPC ........... 514/396; 514/440; 514/444; 424/449; 424/443

(58) Field of Classification Search
None
See application file for complete search history.

(56) References Cited

U.S. PATENT DOCUMENTS

| | | | |
|---|---|---|---|
| 5,229,447 A | 7/1993 | Miyajima et al. | |
| 5,466,820 A | 11/1995 | Itoh et al. | |
| 6,403,063 B1 | 6/2002 | Sawyer | |
| 2002/0004065 A1* | 1/2002 | Kanios | 424/449 |
| 2002/0187181 A1 | 12/2002 | Godbey et al. | |

FOREIGN PATENT DOCUMENTS

| | | |
|---|---|---|
| EP | 0 218 736 | 4/1987 |
| EP | 1 138 314 A2 | 10/2001 |
| JP | 54-140713 | 11/1979 |
| JP | 55-49570 | 12/1980 |
| JP | 60-228412 | 11/1985 |
| JP | 62-093227 | 4/1987 |
| JP | 04-029917 | 1/1992 |
| JP | 07-223971 | 8/1995 |
| JP | 07-277975 | 10/1995 |
| JP | 7-277975 | 10/1995 |
| WO | WO 96/10995 | 4/1996 |
| WO | WO 97/02821 | 1/1997 |

OTHER PUBLICATIONS

Gutierrez-Rocca et al. "Influence of water soluble and insoluble plasticizers on the physical and mechanical properties of acrylic resin copolymers", Int.J.Pharmaceut., 1994, vol. 103, pp. 293-301.*

* cited by examiner

Primary Examiner — James D Anderson
Assistant Examiner — Stephanie Springer
(74) Attorney, Agent, or Firm — Knobbe, Martens, Olson & Bear LLP (57) ABSTRACT

An object of the present invention is to provide a medicinal composition useful for external application in the treatment of a fungal infection reaching the lower part of a thick keratin layer. Provided is an antifungal medicinal composition, comprising: (1) a film-forming agent; (2) a water-soluble plasticizer in a form of a solid or a paste at 20° C. at 1 atm; and (3) an antifungal compound represented by a general formula (1) and/or a physiologically acceptable salt thereof.

7 Claims, 1 Drawing Sheet

ANTIFUNGAL MEDICINAL COMPOSITIONS

RELATED APPLICATIONS

This application is a continuation of U.S. application Ser. No. 10/518,776, filed Dec. 17, 2004 now U.S. Pat. No. 8,039,452, which is the U.S. National Phase under 35 U.S.C. §371 of International Application PCT/JP03/07367, filed Jun. 10, 2003, which was published in a language other than English, which claims priority of JP 2002-177060, filed Jun. 18, 2002.

TECHNICAL FIELD

The present invention relates to a medicinal composition, and more specifically to a medicinal composition useful in the treatment and prevention of fungal diseases.

BACKGROUND ART

Fungal diseases represented by athlete's foot, vaginal candidiasis, and so on were formerly the diseases difficult to be completely cured, so the treatment of athlete's foot has been a theme of eternity.

In recent years, bifonazole and other various drugs such as butenafine and terbinafine have been developed, allowing general cutaneous fungal diseases such as athlete's foot to be completely cured. Among the fungal diseases, however, one invaded in the thickened or excessively keratinized portion of a nail or skin remains almost impossible to be treated with the external application of a drug because of the difficulty of allowing the drug to be transdermally delivered to that portion. Therefore, the treatment of such a fungal disease has been only conducted by means of a method involving orally administering an antifungal agent such as terbinafine for as long as several months. Such oral administration is systemic, so it will involve a great economic burden when it is prolonged. Besides, the above administration has been difficult to be applied on tinea unguium having a little influence on a human life because of an increase in possibility of causing side effects or the like.

In other words, the conventional method has been insufficient to be applied as a therapeutic procedure with external administration of a drug on a fugal disease invaded in the bottom portion of thick keratin such as the inside of a thickened or extensively keratinized portion of a nail or skin. Therefore, development of a medicinal composition useful for an external treatment of the fungal disease invaded in the bottom portion of such thick keratin has been demanded.

On the other hand, the compound represented by the general formula (1) to be described latter has been known to have an antifungal action. However, no technology, which utilizes such a compound as a principal ingredient to prepare an antifungal preparation for tinea unguium or for tinea in the thickened portion of heel or the like, has been known in the art at all.

Furthermore, no idea for obtaining an antifungal medicinal composition by combining the antifungal compound represented by the general formula (1) and a specific film-forming agent or a water-soluble plasticizer in the form of a solid or paste at 20° C. at 1 atm has been known in the art at all. Besides, the fact that the antifungal medicinal composition composed as described above will be useful in the treatment of tinea unguium and the fungal diseases in the excessively keratinized portion or thickened portion of the skin has not been known at all.

DISCLOSURE OF THE INVENTION

The present invention has been made under such circumstances and intends to provide a medicinal composition useful for external application in the treatment of a fungal infection reaching the lower part of a thick keratin layer.

In consideration of such circumstances, the inventors of the present invention have dedicated efforts to the study of obtaining a medicinal composition useful for external application in the treatment of a fungal infection reaching the lower part of a thick keratin layer. Consequently, the inventors of the present invention have completed the present invention by finding out that an antifungal medicinal composition characterized by including (1) a film-forming agent, (2) a water-soluble plasticizer in the form of a solid or a paste at 20° C. at 1 atm, and (3) an antifungal compound represented by the following general formula (1) exert such characteristics.

In other words, the present invention is constructed as described below.

(1) An antifungal medicinal composition, comprising: (1) a film-forming agent; (2) a water-soluble plasticizer in the form of a solid or a paste at 20° C. at 1 atm; and (3) an antifungal compound represented by a general formula (1) and/or a physiologically acceptable salt thereof.

(1)

(In the formula, R represents an alkyl group having 1 to 8 carbon atoms, a cycloalkyl group having 3 to 6 carbon atoms, a methylene group, a lower alkenyl group, a halogen atom, a lower alkyl group substituted with a lower alkoxy group or a lower alkylthio group, or a group represented by a general formula (2) below.)

(2)

(In the formula, $R_1$ represents a hydrogen atom, a halogen atom, a linear- or branched-chain lower alkyl group, a lower alkoxy group, a haloalkoxy group, or a methylenedioxy group, and m represents an integral number of 1 to 3.)

(2) The antifungal medicinal composition according to (1), wherein the firm-forming agent has low water solubility or water insolubility.

(3) The antifungal medicinal composition according to (2), wherein the film-forming agent having low water solubility or water insolubility comprises one or two or more selected from the group consisting of ethyl cellulose, hydroxypropyl methylcellulose phthalate, and an acrylic resin emulsion.

(4) The antifungal medicinal composition according to (2), wherein the film-forming agent having low water solubility or water insolubility comprises ethyl cellulose.

(5) The antifungal medicinal composition according to any one of (1) to (4), wherein the water-soluble plasticizer in the form of a solid or a paste at 20° C. at 1 atm comprises a compound having a polyoxyethylene group and/or a polyoxypropylene group.

(6) The antifungal medicinal composition according to (5), wherein the water-soluble plasticizer in the form of a solid or a paste at 20° C. at 1 atm comprises an oxyethylene oxypropylene copolymer.

(7) The antifungal medicinal composition according to (5), wherein: the film-forming agent having low water solubility or water insolubility comprises one or two or more selected from the group consisting of ethyl cellulose, hydroxypropyl methylcellulose phthalate, and an acrylic resin emulsion; and the water-soluble plasticizer in the form of a solid or a paste at 20° C. at 1 atm comprises a polymer or a copolymer of oxyethylene and/or oxypropylene, and has a polymerization degree of 70 or more.

(8) The antifungal medicinal composition according to any one of (1) to (7), wherein the compound represented by the general formula (1) comprises (E)-[4-(2,4-dichlorophenyl)-1,3-dithiolan-2-ylidene]-1-imidazolyl acetonitrile (Compound 1).

(Compound 1)

(9) The antifungal medicinal composition according to any one of (1) to (8), further comprising a surfactant.
(10) The antifungal medicinal composition according to (9), wherein the surfactant comprises an anionic surfactant.
(11) The antifungal medicinal composition according to (10), wherein the anionic surfactant comprises alkyl sulfate which may have a polyoxyethylene group and/or alkyl phosphate which may have a polyoxyethylene group.
(12) The antifungal medicinal composition according to any one of (1) to (11), further comprising acetone or methyl ethyl ketone as an organic solvent.
(13) The antifungal medicinal composition according to any one of (1) to (12), wherein a coating film having plastic property is formed when the antifungal medicinal composition is applied to an application target.
(14) The antifungal medicinal composition according to (13), wherein the coating film having plastic property shows a glass state having viscosity.
(15) The antifungal medicinal composition according to (13) or (14), wherein the antifungal medicinal composition is capable of recoating.
(16) The antifungal medicinal composition according to any one of (13) to (15), wherein the coating film of the antifungal medicinal composition is removable with swelling means using an aqueous solvent and means for physical scratching.
(17) The antifungal medicinal composition according to any one of (13) to (16), wherein the antifungal medicinal composition is used for an extensively keratinized portion of skin or nail or a skin-thickened portion around foot as an application target.
(18) A method of producing an antifungal medicinal composition having (1) one or two or more selected from the group consisting of ethyl cellulose, hydroxypropyl methylcellulose phthalate, and an acrylic resin emulsion, (2) a polymer or copolymer of oxyethylene and/or oxypropylene, and (3) an antifungal compound represented by a general formula (1) and/or a physiologically acceptable salt thereof, comprising:

dissolving alkyl sulfate which may have a polyoxyethylene group and/or alkyl phosphate which may have a polyoxyethylene group and the polymer or copolymer of oxyethylene and/or oxypropylene in a solvent containing acetone or methyl ethyl ketone;

adding and dissolving in the solution the one or two or more selected from the group consisting of ethyl cellulose, hydroxypropyl methylcellulose phthalate, and an acrylic resin emulsion; and adding and dissolving in the solution the antifungal compound represented by the general formula (1) and/or the physiologically acceptable salt thereof.

(1)

(In the formula, R represents an alkyl group having 1 to 8 carbon atoms, a cycloalkyl group having 3 to 6 carbon atoms, a methylene group, a lower alkenyl group, a halogen atom, a lower alkyl group substituted with a lower alkoxy group or a lower alkylthio group, or a group represented by a general formula (2) below.)

(2)

(In the formula, $R_1$ represents a hydrogen atom, a halogen atom, a linear- or branched-chain lower alkyl group, a lower alkoxy group, a haloalkoxy group, or a methylenedioxy group, and m represents an integral number of 1 to 3.)

BEST MODE FOR CARRYING OUT THE INVENTION

Hereinafter, the present invention will be described in detail.

The antifungal medicinal composition of the present invention is characterized by including (1) a film-forming agent, (2) a water-soluble plasticizer in the form of a solid or a paste at 20° C. at 1 atm, and (3) an antifungal compound represented by the general formula (1) and/or a physiologically acceptable salt thereof.

The film-forming agent in the antifungal medicinal composition of the present invention may be one generally used for medicinal compositions or the like, and preferable examples thereof include one insoluble or poor soluble in water.

Here, the term "insoluble or poor soluble in water" means that the saturated concentration of an agent is about 1 g/10 L, preferably 1 g/50 L or less with reference to water at 20±5° C.

Preferable examples of such a film-forming agent include: alkyl celluloses represented by ethyl cellulose and hydroxypropyl methylcellulose phthalate; and acrylic resin-based emulsions such as one commercially available from Higuchi Shokai Co., Ltd. by the name of Eudragit (registered trademark) NE30D, which is a dispersion liquid of ethyl acrylate/methyl methacrylate copolymer. Each of them may be independently used, or two or more of them may be used in combination. The use of ethyl cellulose alone of those is particularly preferable.

A preferable content of the film-forming agent in the antifungal medicinal composition of the present invention is preferably 0.1 to 10% by weight in volume, more preferably 0.3 to 5% by weight in volume in total with respect to the whole amount of the medicinal composition. This is because a coating film having a sufficient strength cannot be obtained when the amount of the film-forming agent is excessively low and the transfer of a drug may be inhibited when the film-forming agent is provided in an excess amount.

Examples of a water-soluble plasticizer in the form of a solid or a paste at 20° C. at 1 atm, which can be incorporated in the medicinal composition of the present invention, include a polymer or a copolymer of oxyalkylene such as oxyethylene or oxypropylene. A polymer or a copolymer having a larger polymerization degree is preferable. The oxyalkylene is preferably one having 1 to 4 carbon atoms, more preferably oxyethylene and/or oxypropylene.

A preferable polymerization degree of the polyoxyalkylene is preferably 70 or more in total. The polymerization degree is at least 80 or more if there is oxyethylene alone, and is at least 70 or more if there is oxypropylene alone. A preferable combination between oxyethylene and oxypropylene is such that the polymerization degree of oxypropylene is 30 to 80, the polymerization degree of oxyethylene is 35 to 400, and the sum of them is 70 or more.

Copolymers each having oxyethylene and oxypropylene are more preferable. Of those, one having a polyoxyethylene chain having a polymerization degree of 100 to 300 and a polyoxypropylene chain having a polymerization degree of 25 to 80 is still more preferable.

In addition, the oxyalkylene polymer or copolymer may be independently incorporated or may be incorporated in combination with another one. However, when two or more of them are combined, the mixture of such a combination should be kept in the form of a solid or paste at 20° C. at 1 atm.

Of the combinations of the plasticizers, particularly preferable is a copolymer that contains only polyoxyethylene polyoxypropylene ether containing a polyoxyethylene portion having a polymerization degree of 140 to 180 and a polyoxypropylene portion having a polymerization degree of 20 to 40.

A preferable content of the plasticizer in the antifungal medical composition of the present invention is preferably 1 to 10% by weight in volume, more preferably 3 to 8% by weight in volume in total with respect to the whole amount of the medicinal composition.

Furthermore, the content of the plasticizer is preferably 1 to 10 folds, more preferably 3 to 8 folds with respect to the content of the film-forming agent.

The antifungal composition of the present invention is represented by the general formula (1) described above. A compound in which R in the general formula (1) is represented by the general formula (2) is particularly preferable. Concretely, preferable compounds represented by the general formula (1) include (−)-(E)-[4-(2,4-dichlorophenyl)-1,3-dithioran-2-ylidene]-1-imidazolyl acetonitrile (Compound 1), (+)-(E)-[4-(2-chlorophenyl)-1,3-dithioran-2-ylidene]-1-imidazolyl acetonitrile (Compound 2), and lanoconazole. Those compounds are known in the art, and thus the production methods and antifungal characteristics thereof have been already known in the art. JP 62-93227 A can be referred. An optically active substance or a racemic body can be used for such a compound. The optically active substance and the (−) body thereof are particularly preferable.

In addition, the "physiologically acceptable salt thereof" is not specifically limited as far as it is physiologically acceptable, and preferable examples thereof include: mineral acid salts such as hydrochloride, nitrate, sulfate, and phosphate; organic acid salts such as citrate, oxalate, lactate, and acetate; and sulfuric acid-containing acid chlorides such as mesilate and tosylate.

In terms of safety and solubility, hydrochloride is more preferable.

The antifungal compound represented by the general formula (1) and/or a physiologically acceptable salt thereof may be independently used alone or two or more different types thereof may be used in combination.

The content of the antifungal compound represented by the general formula (1) and/or the physiologically acceptable salt thereof in the antifungal medicinal composition of the present invention is preferably 0.1 to 30% by weight in volume, more preferably 0.5 to 15% by weight in volume in total with reference to the total amount of the medicinal composition. The amount of the antifungal compound may be determined in consideration of its relation to the characteristics of a coating film generated.

The medicinal composition of the present invention may include any components generally used in dermatological external preparations in addition to the essential components described above.

Examples of such components include: hydrocarbons such as vaselline and microcrystalline wax; esters such as jojoba oil and spermaceti; triglycerides such as beef tallow and olive oil; higher alcohols such as cetanol and oleyl alcohol; fatty acids such as stearic acid and oleic acid; alcohols such as ethanol and isopropanol; polyvalent alcohols such as glycerine and 1,3-butanediol; water; nonionic surfactants; anionic surfactants; cationic surfactants; amphoteric surfactants; ethanol; thickeners such as carbopol; antiseptics; UV absorbers; antioxidizing agents; pigments; powders; and organic solvents.

Of those, components particularly preferable to be incorporated in the medicinal composition of the present invention include the anionic surfactants and the organic solvents.

In addition, the anionic surfactants are preferable in that each of them has an action of accelerating the penetration of a drug into the nail or the hardened portion of the skin. Each of the anionic surfactants may be used alone or two or more of the anionic surfactants may be used in combination.

Any of sulfate anionic surfactants and phosphorous anionic surfactants can be used as an anionic surfactant, and the anionic surfactant may have a polyoxyethylene chain or not. More preferably, alkyl sulfate which may have a polyoxyethylene group and/or alkyl phosphate which may have a polyoxyethylene group can be mentioned. Alkyl sulfate ester and/or polyoxyethylene-added alkyl triphosphate ester is/are still more preferable. A total number of added moles of the polyoxyethylene is particularly preferably 2 to 16. The alkyl group is preferably one having 10 to 20 carbon atoms. More specifically, preferable examples of the alkyl group include a lauryl group, a palmityl group, and a stearyl group. Particularly preferable examples of a combination of alkyl groups include a configuration containing both lauryl sulfate and tripolyoxyethylene (referred to as triPOE) (4) lauryl ether phosphate. Furthermore, preferable examples of the salts of those anionic surfactants include: alkali metal salts of sodium, potassium, and the like; organic amine salts such as monoethanol amine, triethanol amine, and triethyl amine; ammonium salts; and salts of basic amino acids such as arginine and lysine. Of those, the alkyl metal salts are preferable and sodium salt is particularly preferable.

A preferable content of the anionic surfactant in the antifungal medicinal composition of the present invention is 0.5 to 10% by weight in volume, more preferably 1 to 5% by weight in volume in total with respect to the total amount of the medicinal composition. Particularly preferable is a configuration containing 1 to 5 parts by weight of lauryl sulfate and 0.5 to 3 parts by weight of triPOE(4) lauryl ether phosphate with respect to 100 parts by volume of the antifungal medicinal composition of the present invention.

It is preferable that the antifungal medicinal composition of the present invention contain a polar organic solvent because of an increase in solubility of the antifungal compound represented by the above general formula (1).

Such an organic solvent is preferably one containing ketones, and examples thereof include one containing acetone or methyl ethyl ketone. In particular, an organic solvent containing methyl ethyl ketone is preferable.

A preferable content of the organic solvent in the antifungal medicinal composition of the present invention is 50 to 90% by volume with respect to the total amount of the medicinal composition (hereinafter, the same will be applied). In this composition, a preferable content of the ketones is 10 to 50% by volume. In addition, when an alcohol such as ethanol is additionally included, a preferable content of the alcohol is 20 to 60% by volume.

The medicinal composition of the present invention can be produced by treating the above essential components and arbitrary components in accordance with a usual method.

The medicinal composition thus obtained of the present invention forms a coating film having plastic property when it is applied to an application target. The coating film is in a viscous glass state. More specifically, the coating film itself is in the form of a solid but it is in a state of allowing the components to move inside the coating film.

The coating film is a film on which additional films can be applied. That is, for the purpose of continuing the treatment, when the medicinal composition of the present invention is administered again to form a coating film, the coating film previously applied and dried does not prevent the movement of a drug in the new coating to an affected area.

In addition, when the medicinal composition of the present invention is applied to the affected area of the nail or skin, unlike a conventionally known lacquer preparation, the coating film is hardly removed in general but it can be removed by swelling means using an aqueous solvent and means for physically scratching the coating film. Concretely, under a humidity condition with water or the like, the coating film made of the medicinal composition of the present invention can be easily removed by scratching the coating film with an applied surfactant such as soap as required.

Furthermore, the coating film is in a glass state, so the movement of a drug from the coating film to the affected area can easily occur. As a result, the drug can be always supplied to the affected area at a predetermined concentration. Therefore, the drug availability rises as compared to the normal lacquer preparation. For this reason, the antifungal medicinal composition of the present invention can be effectively used as external application for the treatment of fungal diseases in the excessive keratinized portion of the skin and the thickened portion of the skin around the foot where the administration effect of the general antifungal medicinal composition for external application is hardly obtained. Consequently, the antifungal medicinal composition of the present invention can be used to the affected area of the excessive keratinized portion of the nail or skin, or the thickened skin portion around the foot.

Furthermore, fungi to be targeted with the antifungal medicinal composition of the present invention include *Trichophyton* (*Trichophyton*), a causative organism of candidiasis (*Candida*), a causative organism of cryptospolidiosis (*cryptosporidium*), and yeasts (*Aspergillus*).

The medicinal composition of the present invention can be produced by means of the general procedures. A preferable production example in a preferred embodiment will be described below.

For the production of an antifungal medicinal composition including: (1) one or two or more selected from the group consisting of ethyl cellulose, hydroxypropyl methylcellulose phthalate, and an acrylic resin emulsion; (2) a polymer or copolymer composed of oxyethylene and/or oxypropylene, and (3) an antifungal compound represented by the general formula (1) and/or a physiologically acceptable salt thereof, alkyl sulfate which may have a polyoxyethylene group and/or alkyl phosphate which may have a polyoxyethylene group and the polymer or copolymer composed of oxyethylene and/or oxypropylene are dissolved in a solvent containing acetone or methyl ethyl ketone. In this solution, furthermore, the one or two or more selected from the group consisting of ethyl cellulose, hydroxypropyl methylcellulose phthalate, and an acrylic resin emulsion is/are added and dissolved, followed by adding and dissolving the antifungal compound represented by the general formula (1) and/or the physiologically acceptable salt thereof. The production according to such a method allows the pharmaceutical manufacturing of the antifungal composition represented by the general formula (1) in a stable manner without causing crystal even in the case of using a water-containing solvent.

Consequently, a preferable production method of the antifungal medicinal composition of the present invention can be provided.

EXAMPLES

Hereinafter, the present invention will be described concretely with reference to examples. However, the present invention is not limited to these examples.

Furthermore, the abbreviations in each of examples and tables represent the following.
HP-55: Hydroxypropyl methylcellulose phthalate
Pluronic F-68: Polyoxyethylene (160) polyoxypropylene (30) glycol
Macrogol 200: Polyethylene glycol 200
SDS: Sodium lauryl sulfate
TLP-4: Tripolyoxyethylene (4) lauryl ether sodium phosphate Example 1

According to the formulation shown in Table 1 below, the antifungal medicinal composition of the present invention was produced. The components a were stirred and solubilized. Then, the component b was added and solubilized, and the component c was further added and solubilized, followed by the addition of the component d. Subsequently, the component e was added in order to adjust the pH of the mixture to pH 6, followed by the addition of the component f to make the total volume up to 100 ml. Consequently, an antifungal medicinal composition was obtained.

TABLE 1

| | Components | |
|---|---|---|
| a | Methyl ethyl ketone | 35 mL |
| | Ethanol | 35 mL |
| | Pluronic F-68 | 5 g |
| | Sodium lauryl sulfate | 2 g |
| b | Ethyl cellulose | 1 g |
| c | Compound 1 | 2 g |
| d | Water | 15 g |
| e | Phosphoric acid | Optimum dose |
| f | Ethanol | Making total volume up to 100 ml |

Examples 2 to 4

The components a to f were added in the same order as that of Example 1 to prepare antifungal compositions of the present invention shown in Table 2 below. In addition, as shown in Table 2, comparative examples of the comparable technologies which did not belong to the antifungal medicinal composition of the present invention were also prepared.

TABLE 2

| Components | | Example 2 | Example 3 | Example 4 | Comparative Example 1 | Comparative Example 2 | Comparative Example 3 | Comparative Example 4 | Comparative Example 5 | Comparative Example 6 |
|---|---|---|---|---|---|---|---|---|---|---|
| a | Methyl ethyl ketone | 35 mL | 10 mL | 10 ml | 25 mL | 35 mL | 35 mL | 35 mL | 10 mL | 10 mL |
| | Pluronic F-68 | 5.0 g | 5.0 g | 5.0 g | 5.0 g | — | — | — | — | — |
| | Macrogol 200 | — | — | — | — | — | 5.0 g | — | — | — |
| | Octyl dodecanol | — | — | — | — | — | — | 5.0 g | — | — |
| | SDS | — | 2.0 g | — | 2.0 g | — | — | — | 2.0 g | — |
| | TLP-4 | 1.0 g | — | 1.0 g | — | 1.0 g | 1.0 g | 1.0 g | — | 1.0 g |
| b | Ethyl cellulose | 1.0 g | 4.0 g | — | — | 1.0 g | 1.0 g | 1.0 g | 4.0 g | — |
| | HP-55 | — | — | 4.0 g | — | — | — | — | — | 4.0 g |
| c | Compound 1 | 5.0 g | 1.0 g | 1.0 g | 2.0 g | 5.0 g | 5.0 g | 5.0 g | 1.0 g | 1.0 g |
| d | Purified water | 15.0 g | 15.0 g | 15.0 g | 15.0 g | 15.0 g | 15.0 g | 15.0 g | 15.0 g | 15.0 g |
| e | Phosphoric acid (adjusted to pH 6) | Optimum dose | Optimum dose | Optimum dose | Optimum dose | Optimum dose | Optimum dose | Optimum dose | Optimum dose | Optimum dose |
| a, f | Absolute ethanol | Optimum dose | Optimum dose | Optimum dose | Optimum dose | Optimum dose | Optimum dose | Optimum dose | Optimum dose | Optimum dose |
| | Total | 100 mL | 100 mL | 100 mL | 100 mL | 100 mL | 100 mL | 100 mL | 100 mL | 100 mL |

Example 5

The antifungal medicinal compositions for external application of the present invention of Examples 1 to 4 and the antifungal medicinal compositions for external application of Comparative Examples 1 to 6 were investigated for characteristics of a coating film resulting from the application on nails.

As for the characteristics of the coating film, evaluation items were defined as: a time period (second) from the drying after application to the film formation; the condition of the coating film at 12 hours from the application; and the removability of the coating film with water at 12 hours from the application, respectively.

The criteria for the coating film conditions were
◎: no removal of the coating film;
○: partial removal of the coating film;
Δ: almost half removal of the coating film; and
×: more than half removal of the coating film.
The criteria for the removability were
◎: easily washing out the coating film;
○: requiring scouring to wash out the coating film; and
×: impossible to wash out the coating film by means of running water.

The results are shown in Table 3. The results show that the antifungal external application of the present invention is excellent in retaining the coating film while the coating film can be easily removed through water washing

TABLE 3

| Sample | Drying time | Conditions after 12 hours | Washing efficiency |
|---|---|---|---|
| Example 1 | 45 seconds | ◎ | ◎ |
| Example 2 | 40 seconds | ◎ | ◎ |
| Example 3 | 65 seconds | ◎ | ◎ |
| Example 4 | 67 seconds | ◎ | ◎ |
| Comparative Example 1 | 40 seconds | × | ◎ |
| Comparative Example 2 | 50 seconds | ◎ | × |
| Comparative Example 3 | 50 seconds | × | ○ |
| Comparative Example 4 | 60 seconds | × | ○ |
| Comparative Example 5 | 60 seconds | ◎ | × |

TABLE 3-continued

| Sample | Drying time | Conditions after 12 hours | Washing efficiency |
|---|---|---|---|
| Comparative Example 6 | 50 seconds | ◎ | × |

Example 6

The antifungal medicinal compositions for external preparation of Examples 3 and 4 described above and the antifungal medicinal compositions for external preparation of Comparative Examples 5 and 6 described above were investigated in terms of the drug release from their coating films formed using a Franz type diffusion cell.

Figure 1:
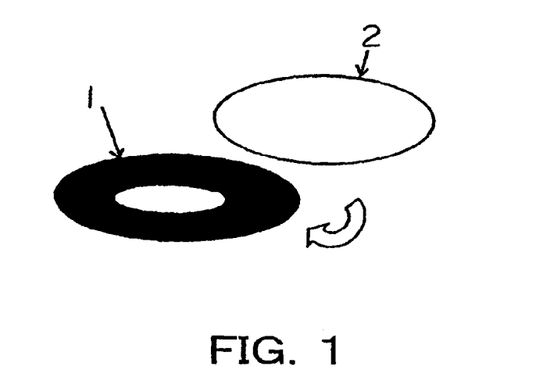
FIG. 1 is a diagram showing a sample charge of a Franz type cell.

As shown in FIG. 1, 200 μl of a pharmaceutical agent were dropped onto a PET sheet (reference numeral 1) to form a coating film and then a dialysis membrane (reference numeral 2) was laminated on this sheet. The dialysis membrane was directed to a receptor and then mounted on the Franz type diffusion cell. Subsequently, the receptor was filled with 0.01 N hydrochloric acid and samples were then obtained from the receptor at regular time intervals to determine the level of the pharmaceutical agent in the liquid in the receptor using HPLC.

Figure 2:
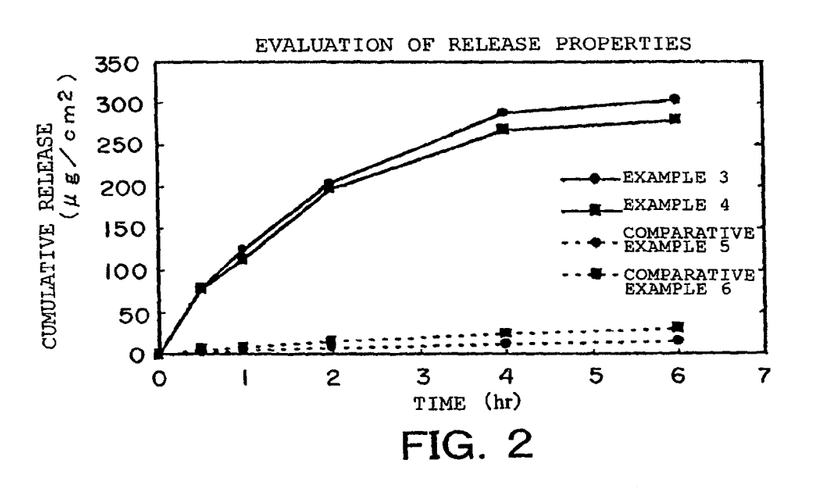
FIG. 2 is a diagram representing the results of Example 6.

The results are shown in FIG. 2. As is evident from FIG. 2, the compositions of Examples 3 and 4 have excellent characteristics of drug release compared with those of Comparative Examples 5 and 6.

In consideration of those results together with the results of the above examples, it is found that the antifungal medicinal composition of the present invention keeps a drug-storing film intact over an extended time period and releases the drug from the film effectively to enhance the therapeutic effects of the drug, while it retains the ability of being easily removed when it is needed to be removed.

Example 7

In Vitro Test for Pharmacometrics

A cylindrical silicone ring was fixed on the surface of nail plate (human) with a silicon bond, and the resultant was placed on a nutrient-free agar medium containing $2\times10^5$/ml of conidiospores of *Trichophyton mentagrophytes*, followed by incubating the medium at 28° C. for 7 days.

After incubation, the growth of bacteria on the nail bed side was confirmed and then each agent, 51, was administered in the cylindrical ring. After administration, the resultant was incubated at 28° C. for 7 days and then the nail was removed from the medium, followed by lightly scratching the nail bed side with a needle spreader.

On this occasion, the nail waste caused was seeded on a Sabouraud's agar medium and then incubated at 28° C. for 14 days, followed by confirming the bacterial growth. The nail, which did not show the bacterial growth, was recognized as bacteria negative. The ratio (%) of the bacteria negative nail waste was determined. The results are shown in Table 4.

As is evident from the results, the antifungal medicinal composition of the present invention exerts excellent abilities of storing and releasing a drug and also exerts excellent effects on fungal diseases which are hardly cured by means of the general external application therapy owing to the inhibition of thick keratin such as a nail.

TABLE 4

| | Example 2 | Comparative Example 2 | Comparative Example 4 |
|---|---|---|---|
| Name of drug | Compound 1 | Compound 1 | Compound 1 |
| Level of drug | 5% | 5% | 5% |
| Bacterial negative ratio (n = 6) | 100% | 33.3% | 33.3% |

Examples 8 and 9

The components a to f (except e) were added in the same order as that of Examples 1 to 4 to prepare the antifungal medicinal compositions (Examples 8 and 9) of the present invention shown in Table 5 below. In addition, as shown in Table 5, the antifungal medicinal compositions of Comparative Examples 7 to 9 were prepared.

Those compositions were investigated for drying time and conditions and washing efficiency after 12 hours. The results were shown in Table 6.

TABLE 5

| Components | | Example 8 | Example 9 | Comparative Example 7 | Comparative Example 8 | Comparative Example 9 |
|---|---|---|---|---|---|---|
| a | Methyl ethyl ketone | 35 mL | 35 mL | 35 mL | 35 mL | 35 mL |
| | Pluronic F-68 | 5 g | 3 g | | | 5 g |
| | SDS | 2 g | 0 g | 2 g | 0 g | 2 g |
| b | Ethyl cellulose | 1.5 g | 0 g | 1.5 g | 0 g | 1.5 g |
| | Ethy lacrylate/methyl methacrylate copolymer dispersion (solid) | | 1.5 g | | 1.5 g | |
| c | Lanoconazole | 2.0 g | 2.0 g | 2.0 g | 2.0 g | 0 g |
| d | Purified water | 15 g | 15 g | 15 g | 15 g | 15 g |
| a, f | Absolute ethanol | Optimum dose | Optimum dose | Optimum dose | Optimum dose | Optimum dose |
| | Total | 100 mL | 100 mL | 100 mL | 100 mL | 100 mL |

TABLE 6

| Sample | Drying time | Conditions after 12 hours | Washing efficiency |
|---|---|---|---|
| Example 8 | 40 seconds | ☉ | ☉ |
| Example 9 | 50 seconds | ☉ | ☉ |
| Comparative Example 7 | 40 seconds | ☉ | X |
| Comparative Example 8 | 50 seconds | ☉ | X |
| Comparative Example 9 | 40 seconds | ☉ | X |

Example 10

The in vitro effects of the antifungal medicinal composition of the present invention were evaluated by the same way as that of Example 7, except that incubation was carried out at 28° C. for 14 days. The results are shown in Table 7.

Therefore, it is evident that the medicinal composition of the present invention has an excellent antifungal action. In addition, it is also found that the compounds represented by the general formula (1), in particular Compound 1, are particularly preferable for a pharmaceutical preparation.

TABLE 7

|  | Example 1 | Example 8 | Comparative Example 9 |
|---|---|---|---|
| Name of drug | Compound 1 | Lanoconazole | None |
| Level of drug | 2% | 2% | None |
| Bacterial negative ratio (n = 6) | 100% | 83.3% | 0% |

Example 11

The medicinal composition of the present invention was prepared by the same way as that described above, except that the concentration of Compound 1 was changed.

TABLE 8

| | Components | |
|---|---|---|
| a | Methyl ethyl ketone | 35 mL |
| | Ethanol | 35 mL |
| | Pluronic F-68 | 5 g |
| | Sodium lauryl sulfate | 2 g |
| b | Ethyl cellulose | 1 g |
| c | Compound 1 | 5 g |
| d | Water | 15 g |
| e | Phosphoric acid | Optimum dose |
| f | Ethanol | Making total volume up to 100 ml |

Example 12

The medicinal composition of the present invention was prepared by the same way as that described above, except that the concentration of Compound 1 was changed.

TABLE 9

| | Components | |
|---|---|---|
| a | Methyl ethyl ketone | 35 mL |
| | Ethanol | 35 mL |
| | Pluronic F-68 | 5 g |
| | Sodium lauryl sulfate | 2 g |
| b | Ethyl cellulose | 1 g |
| c | Compound 1 | 2.5 g |
| d | Water | 15 g |
| e | Phosphoric acid | Optimum dose |
| f | Ethanol | Making total volume up to 100 ml |

Example 13

The medicinal composition of the present invention was prepared by the same way as that described above, except that the concentration of Compound 1 was changed.

TABLE 10

| | Components | |
|---|---|---|
| a | Methyl ethyl ketone | 35 mL |
| | Ethanol | 35 mL |
| | Pluronic F-68 | 5 g |
| | Sodium lauryl sulfate | 2 g |
| b | Ethyl cellulose | 1 g |
| c | Compound 1 | 1.25 g |
| d | Water | 15 g |

TABLE 10-continued

| | Components | |
|---|---|---|
| e | Phosphoric acid | Optimum dose |
| f | Ethanol | Making total volume up to 100 ml |

Example 14

Reference Examples, in which the medicinal compositions of Examples 11 to 13 described above and Compound 1 of Example 11 were substituted with ethanol respectively, were subjected to a primary skin irritation test.

That is, the backs of rabbits (New Zealand White species, six animals per group) were dehaired to form 6 areas of 3 cm×3 cm. On each of those areas, a lint cloth soaked with 0.5 ml of the sample was pasted and then covered with Parafilm and a bandage, followed by conducting a 24-hour closed patch. One of the areas was not patched and treated. At one hour after removal of the patch, a skin reaction was observed in terms of two items: (1) erythema and crust formation and (2) edema formation.

The erythema and crust formation were evaluated on the basis of the following evaluation criteria/

Score 0: no erythema, Score 1: minimum erythema, Score 3: clear erythema, and Score 4 middle to strong erythema, mild crust formation in erythema with strong dark red.

The edema formation was evaluated on the basis of the following criteria.

Score 0: no edema, Score 1: minimum edema; Score 2, clear edema, Score 3: medium edema, and Score 4: strong edema.

The results show that any of the sampled areas was Score 0 for each of (1) erythema and crust formation and (2) edema formation. As is evident from those results, the safety in dermatological external application of the present invention was confirmed.

INDUSTRIAL APPLICABILITY

According to the present invention, a medicinal composition useful for external application in the treatment of a fungal infection reaching the lower part of a thick keratin layer can be provided.

What is claimed is:

1. An antifungal medicinal composition, comprising:
   (1) a film-forming agent which comprises ethyl cellulose;
   (2) a water-soluble plasticizer selected from the group consisting of an oxyethylene oxypropylene copolymer, triethyl citrate, and diethylene glycol monoethyl ether; and
   (3) an antifungal compound represented by general formula (1) and/or a physiologically acceptable salt thereof,
   wherein the ratio of weight of the water soluble plasticizer and the film forming agent is from 1:1 to 10: 1 and
   wherein the final film after application is a glass;

(1)

wherein R represents an alkyl group having 1 to 8 carbon atoms, a cycloalkyl group having 3 to 6 carbon atoms, a methylene group, a lower alkenyl group, a halogen atom, a lower alkyl group substituted with a lower alkoxy group or a lower alkylthio group, or a group represented by general formula (2), (2)

wherein $R_1$ represents a hydrogen atom, a halogen atom, a linear- or branched-chain lower alkyl group, a lower alkoxy group, a haloalkoxy group, or a methylenedioxy group, and m represents an integer from 1 to 3.

2. The antifungal medicinal composition according to claim 1, wherein: the water-soluble plasticizer comprises an oxyethylene oxypropylene copolymer, and the copolymer has a polymerization degree of 70 or more.

3. The antifungal medicinal composition according to claim 1, wherein the compound represented by general formula (1) comprises (E)[4-(2,4-dichlorophenyl)-1,3-dithiolan-2-ylidene]-1-imidazolyl acetonitrile (Compound 1)

(Compound 1)

4. The antifungal medicinal composition according claim 1, further comprising a surfactant.

5. The antifungal medicinal composition according to claim 4, wherein the surfactant comprises an anionic surfactant.

6. The antifungal medicinal composition according to claim 5, wherein the anionic surfactant comprises one or more selected from the group consisting of alkyl sulfate, alkyl sulfate having a polyoxyethylene group, alkyl phosphate, and alkyl phosphate having a polyoxyethylene group.

7. The antifungal medicinal composition according to claim 1, further comprising acetone or methyl ethyl ketone as an organic solvent.

* * * * *

UNITED STATES PATENT AND TRADEMARK OFFICE
CERTIFICATE OF CORRECTION

PATENT NO. : 8,741,941 B2  Page 1 of 1
APPLICATION NO. : 13/240833
DATED : June 3, 2014
INVENTOR(S) : Hideaki Sasagawa et al.

It is certified that error appears in the above-identified patent and that said Letters Patent is hereby corrected as shown below:

In the Specification

In column 1 at line 41 (approx.), Change "fugal" to --fungal--.

In column 6 at line 11, Change "mesilate" to --mesylate--.

In column 6 at line 33, Change "vaselline" to --vaseline--.

In column 8 at line 8, Change "cryptospolidiosis" to --cryptosporidiosis--.

In column 10 at line 4, Change "washing" to --washing.--.

In column 12 (Table 5) at line 8, Change "Ethy lacrylate/" to --Ethyl acrylate/--.

In column 14 at line 24 (approx.), Change "criteria/" to --criteria.--.

In the Claims

In column 15 at line 23, In Claim 3, after "by" insert --the--.

In column 16 at line 12, In Claim 4, after "according" insert --to--.

Signed and Sealed this
Tenth Day of February, 2015

Michelle K. Lee
*Deputy Director of the United States Patent and Trademark Office*